(12) United States Patent
English et al.

(10) Patent No.: US 12,728,271 B2
(45) Date of Patent: Sep. 8, 2026

(54) HEADER SPLITLINE FEATURE

(71) Applicant: Cardiac Pacemakers, Inc., St. Paul, MN (US)

(72) Inventors: James Michael English, Cahir (IE); Moira B. Sweeney, St. Paul, MN (US); Jamie Murphy, Abbeyfeale (IE); Michael Dunne, Castlecomer (IE); Daragh Nolan, Via Youghal (IE); Michael J. Kane, St Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 238 days.

(21) Appl. No.: 18/390,728

(22) Filed: Dec. 20, 2023

(65) Prior Publication Data

US 2024/0226585 A1 Jul. 11, 2024

Related U.S. Application Data

(60) Provisional application No. 63/438,199, filed on Jan. 10, 2023.

(51) Int. Cl.
*A61N 1/375* (2006.01)

(52) U.S. Cl.
CPC ....... *A61N 1/3752* (2013.01); *A61N 1/37512* (2017.08); *A61N 1/3758* (2013.01)

(58) Field of Classification Search
CPC .. A61N 1/375; A61N 1/3752; A61N 1/37512; A61N 1/3758
See application file for complete search history.

(56) References Cited

U.S. PATENT DOCUMENTS

| | | | | |
|---|---|---|---|---|
| 8,690,609 | B2 * | 4/2014 | Poon | H01R 24/58 439/668 |
| 12,161,873 | B2 * | 12/2024 | Carter | A61B 18/1485 |
| 2008/0255631 | A1 * | 10/2008 | Sjostedt | A61N 1/3752 607/37 |
| 2014/0330346 | A1 * | 11/2014 | Sharma | A61N 1/3754 607/60 |
| 2021/0187306 | A1 | 6/2021 | Spadgenske et al. | |
| 2022/0047876 | A1 | 2/2022 | Becklund et al. | |

* cited by examiner

*Primary Examiner* — Brian T Gedeon
(74) *Attorney, Agent, or Firm* — Nelson Mullins Riley & Scarborough LLP

(57) ABSTRACT

An implantable medical device can include a housing including electronic devices within the housing, and a header attached to the housing. The header can include a first silicone portion configured to surround a first portion of internal electronics of the header, and a second silicone portion configured to surround a second portion of internal electronics of the header. The header can further include a splitline where the first silicone portion abuts the second silicone portion, wherein an outer edge of the first silicone portion and an outer edge of the second silicone portion are rounded at the splitline to prevent a sharp edge that may cause damage during assembly or insertion.

20 Claims, 7 Drawing Sheets

404
414
406
402
412

440

400

HEADER SPLITLINE FEATURE

CLAIM OF PRIORITY

This application claims the benefit of U.S. Provisional Application No. 63/438,199, filed on Jan. 10, 2023, which is hereby incorporated by reference in its entirety.

TECHNICAL FIELD

Various embodiments described herein relate to apparatus, systems, and methods associated with headers of implantable medical devices.

BACKGROUND

An ambulatory medical device, such as an implantable medical device (IMD), can be configured for implant in a subject, such as a patient. An IMD can be configured to be coupled to a patient's heart such as via one or more implantable leads. Such an IMD can obtain diagnostic information or generate therapy to be provided to the patient, such as via the coupled implantable lead.

In one configuration, IMDs have a header that is coupled to a container that houses much of the electronics of the IMD. The header can be used to couple a conductor of the lead with circuitry within the implantable device. In some examples, the header may include multiple silicone portions that mate together. However, the area where the silicone portions meet may form a sharp edge that can cause damage upon insertion.

SUMMARY

Systems and methods are disclosed to provide a splitline feature for a header of an implantable medical device.

An example (e.g., "Example 1") of subject matter (e.g., a header for a medical device, etc.) may comprise a first silicone portion configured to surround a first portion of internal electronics of the header; a second silicone portion configured to surround a second portion of internal electronics of the header; and a splitline where the first silicone portion abuts the second silicone portion, wherein an outer edge of the first silicone portion and an outer edge of the second silicone portion are rounded at the splitline.

In Example 2, the subject matter of Example 1 may optionally be configured such that the outer edge of the first silicone portion and the outer edge of the second silicone portion are rounded to a radius of greater than 8 thou at the splitline.

In Example 3, the subject matter of any one or more of Examples 1-2 may optionally be configured such that the outer edge of the first silicone portion and the outer edge of the second silicone portion are rounded to a radius of greater than 10 thou at the splitline.

In Example 4, the subject matter of any one or more of Examples 1-3 may optionally be configured such that the outer edge of the first silicone portion and the outer edge of the second silicone portion are rounded to a radius of greater than 15 thou at the splitline.

In Example 5, the subject matter of any one or more of Examples 1~4 may optionally be configured such that the outer edge of the first silicone portion and the outer edge of the second silicone portion are indented at the splitline.

In Example 6, the subject matter of any one or more of Examples 1-5 may optionally be configured such that the outer edge of the first silicone portion and the outer edge of the second silicone portion are machined at the splitline.

In Example 7, the subject matter of any one or more of Examples 1-6 may optionally be configured such that the outer edge of the first silicone portion and the outer edge of the second silicone portion including a radius undercut feature at the splitline.

An example (e.g., "Example 8") of subject matter (e.g., an implantable medical device, etc.) may comprise a housing including electronic devices within the housing; and a header attached to the housing, the header including: a first silicone portion configured to surround a first portion of internal electronics of the header; a second silicone portion configured to surround a second portion of internal electronics of the header; and a splitline where the first silicone portion abuts the second silicone portion, wherein an outer edge of the first silicone portion and an outer edge of the second silicone portion are rounded at the splitline.

In Example 9, the subject matter of Example 8 may optionally be configured such that the outer edge of the first silicone portion and the outer edge of the second silicone portion are rounded to a radius of greater than 8 thou at the splitline.

In Example 10, the subject matter of any one or more of Examples 8-9 may optionally be configured such that the outer edge of the first silicone portion and the outer edge of the second silicone portion are rounded to a radius of greater than 10 thou or 15 thou at the splitline.

In Example 11, the subject matter of any one or more of Examples 8-10 may optionally be configured such that the outer edge of the first silicone portion and the outer edge of the second silicone portion are indented at the splitline.

In Example 12, the subject matter of any one or more of Examples 8-11 may optionally be configured such that the outer edge of the first silicone portion and the outer edge of the second silicone portion are machined at the splitline.

In Example 13, the subject matter of any one or more of Examples 8-12 may optionally be configured such that the outer edge of the first silicone portion and the outer edge of the second silicone portion including a radius undercut feature at the splitline.

In Example 14, the subject matter of any one or more of Examples 8-13 may optionally be configured such that the header is configured to contact a surface of the housing during a curing or hardening process.

An example (e.g., "Example 15") of subject matter (e.g., a method of assembling a header for a medical device) may comprise providing a first silicone portion configured to surround a first portion of internal electronics of the header; providing a second silicone portion configured to surround a second portion of internal electronics of the header; and placing the first silicone portion against the second silicone portion at a splitline, wherein an outer edge of the first silicone portion and an outer edge of the second silicone portion are rounded at the splitline.

In Example 16, the subject matter of Example 15 may optionally be configured such that the outer edge of the first silicone portion and the outer edge of the second silicone portion are rounded to a radius of greater than 8 thou at the splitline.

In Example 17, the subject matter of any one or more of Examples 15-16 may optionally be configured such that the outer edge of the first silicone portion and the outer edge of the second silicone portion are rounded to a radius of greater than 10 thou at the splitline.

In Example 18, the subject matter of any one or more of Examples 15-17 may optionally be configured such that the outer edge of the first silicone portion and the outer edge of the second silicone portion are rounded to a radius of greater than 15 thou at the splitline.

In Example 19, the subject matter of any one or more of Examples 15-18 may optionally be configured such that the outer edge of the first silicone portion and the outer edge of the second silicone portion are indented at the splitline.

In Example 20, the subject matter of any one or more of Examples 15-19 may optionally be configured such that the outer edge of the first silicone portion and the outer edge of the second silicone portion are machined at the splitline.

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

DETAILED DESCRIPTION

In the following detailed description, reference is made to the accompanying drawings that form a part hereof and in which are shown, by way of illustration, specific embodiments in which the invention may be practiced. These embodiments are described in sufficient detail to enable those skilled in the art to practice the invention. Other embodiments may be utilized and structural, logical, and electrical changes may be made.

Figure 1:
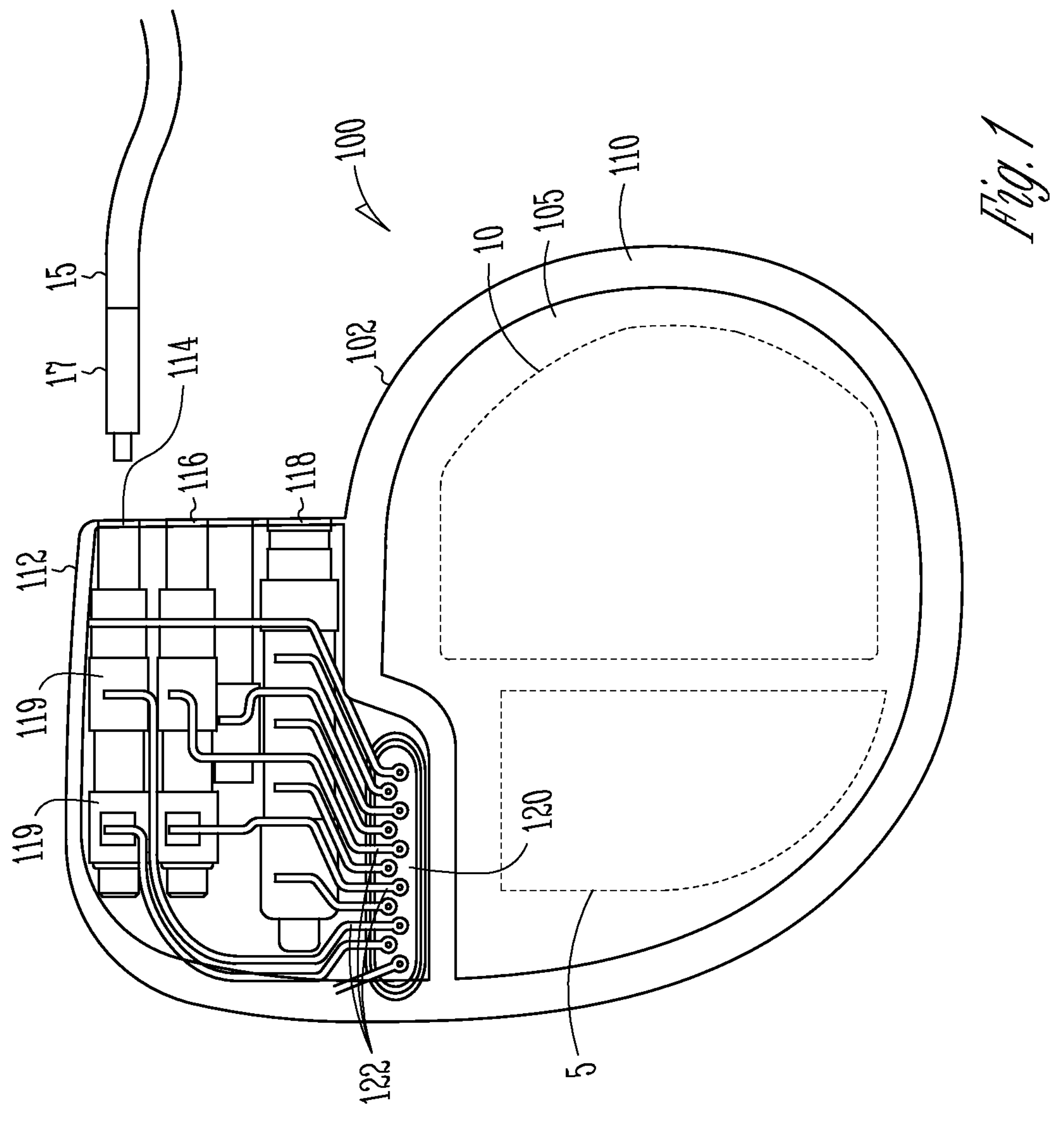
FIG. 1 shows an example implantable medical device, in accordance with one embodiment.

FIG. 1 shows an implantable system 100 including an implantable medical device 102, in accordance with one embodiment. The implantable medical device 102 includes a pulse generator 105 and at least one implantable lead 15. The pulse generator 105 includes a housing 110 and a header 112 mounted to the housing 110. The pulse generator 105 can be implanted into a subcutaneous pocket made in the wall of a patient's chest. Alternatively, the pulse generator 105 can be placed in a subcutaneous pocket made in the abdomen, or in other locations. Pulse generator 105 can include electronic devices such as a power supply 5 including a battery, a capacitor, and other components housed in the housing 110. The pulse generator 105 can further include other electronic devices such as microprocessors 10 to provide processing, evaluation, and to deliver electrical shocks and pulses of different energy levels and timing for defibrillation, cardioversion, and pacing to a heart in response to cardiac arrhythmia including fibrillation, tachycardia, heart failure, and bradycardia.

The header 112 can include one or more bores 114, 116, 118 to receive an implantable lead 15. The implantable lead 15 can include electrodes on a distal end to provide therapy to a body and include a connector pin 17 on the proximal end to couple to the bore 114, 116, 118. At least one electrical conductor is disposed within the lead 15 and extends from the proximal end to the electrode. The electrical conductor carries electrical currents and signals between the pulse generator 105 and the distal electrode.

Contacts on the connector pin 17 can electrically contact electrical contacts 119 within the bores 114, 116, 118 to allow signals and therapy to be delivered to and from the electrodes in a body to the electronics 5, 10 within the housing 110. The contacts 119 can be connected by wires 122 to a feedthrough assembly 120 to electrically communicate between the lead 15 and the electronics within the housing 110.

In one example, the header 112 can be formed from a polymer material. A polymer can provide a number of desirable features, such as biocompatibility, strength, resilience, and ease of manufacturing. In one example, the header 112 is molded separately from the housing 110, and later bonded to the housing 110 using an adhesive. In a second example, the header 112 can be molded in place (overmolded) and contacts a surface of the housing 110 during a curing or hardening process.

In this example, the implantable medical device 102 includes an antenna 130 extending from the housing 110 into the header 112. The antenna 130 can be coupled on one end to a feedthrough assembly 120 attached to the housing 110. The other end of the antenna 130 extends into the header 112.

In other embodiments, the implantable system 100 can also be suitable for use with implantable electrical stimulators, such as, but not limited to, neuro-stimulators, skeletal stimulators, central nervous system stimulators, or stimulators for the treatment of pain.

In this example, the header 112 can be molded in place and contacts a surface of the housing 110 during a curing or hardening process. In some examples, the header may include multiple silicone portions that mate together. As noted above, during manufacture it is important to prevent or avoid sharp edges along the area where the silicone portions meet that can cause damage upon assembly or insertion.

Figure 2A:
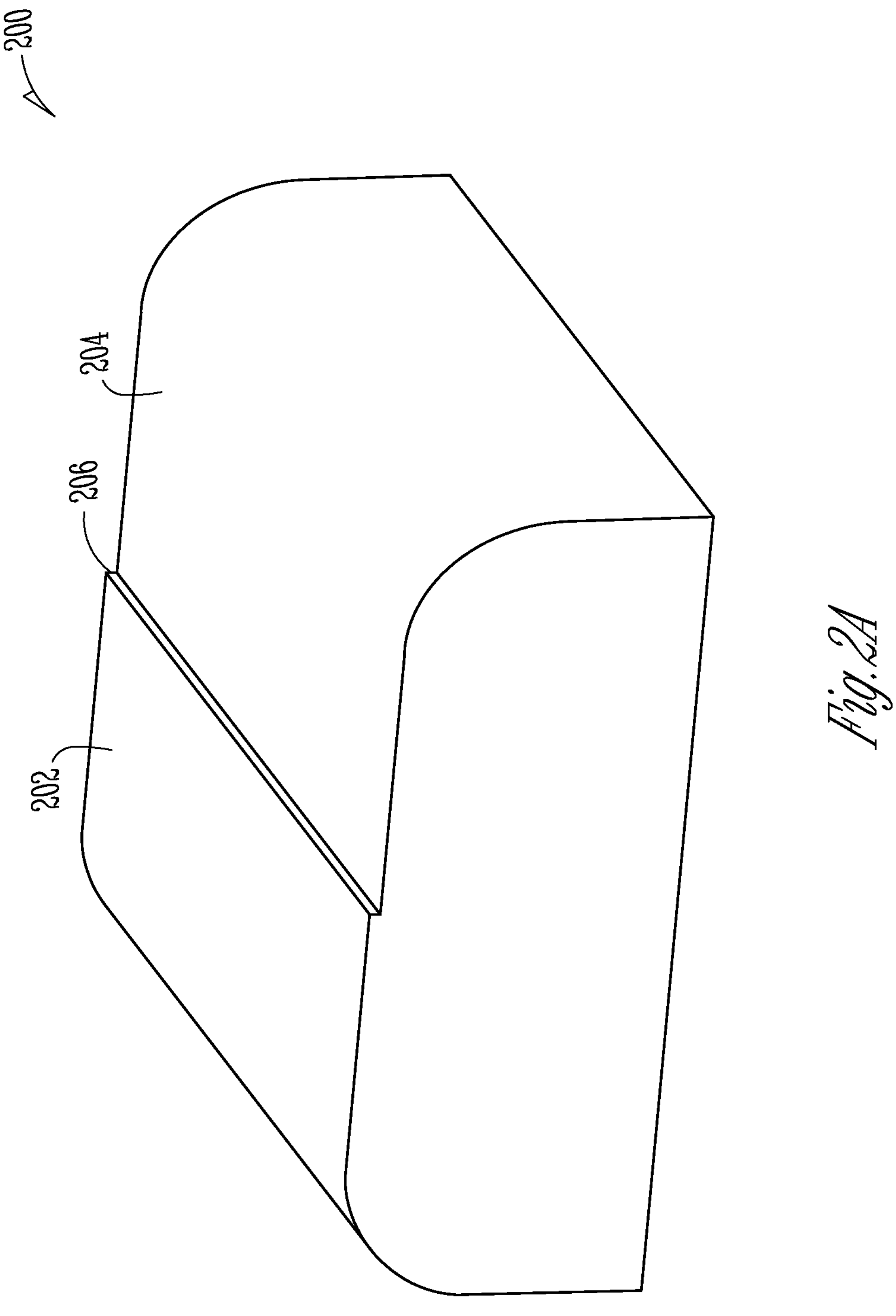
FIGS. 2A-2B show a portion of a header of an implantable medical device.
Figure 2B:
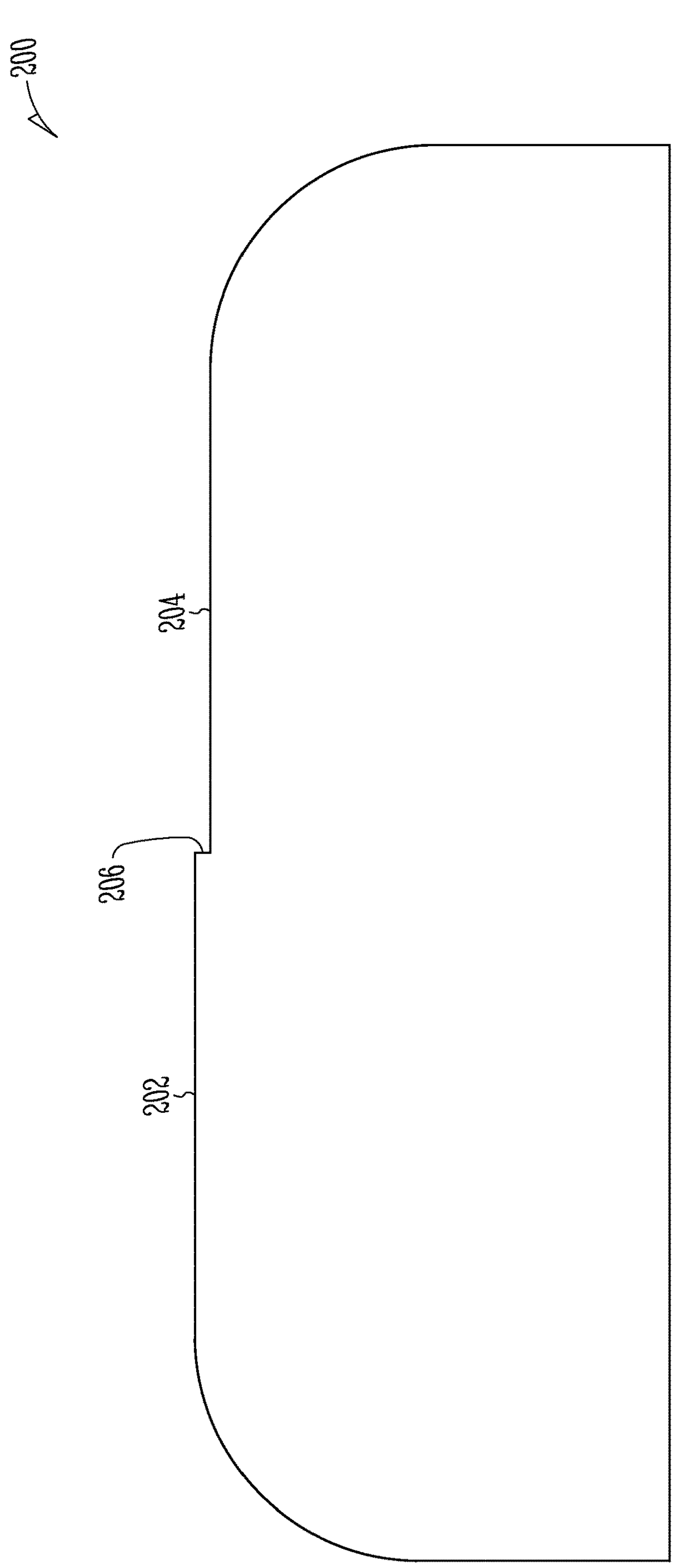

FIGS. 2A-2B show a portion of a header of an implantable medical device. In these views, the device is shown without the header of the present subject matter for reference. Instead, this view shows a header 200 including a first silicone portion 202 configured to surround a first portion of internal electronics of the header, and a second silicone portion 204 configured to surround a second portion of internal electronics of the header. The header 200 can further include a splitline 206 where the first silicone portion abuts the second silicone portion. The area where the two silicone portions 202, 204 meet, or the splitline 206, includes a sharp edge that may cause damage during assembly or insertion. These views show the sharp edge on the current state of art headers, including a sharp 90 degree step down in the middle of the part at the splitline 206.

Figure 3A:
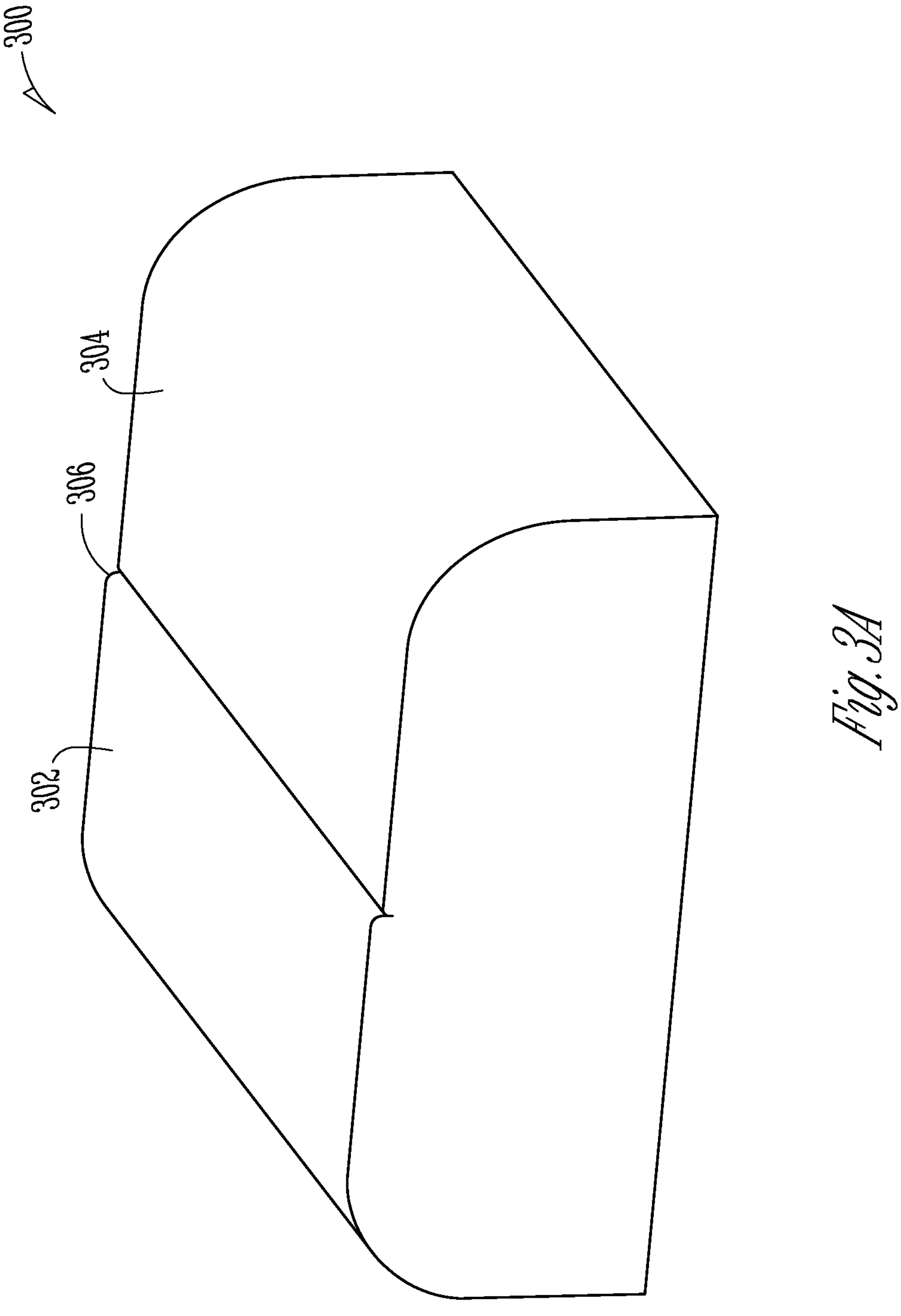
FIGS. 3A-3B show a portion of a header of an implantable medical device, in accordance with one embodiment.
Figure 3B:
Figure 3B:
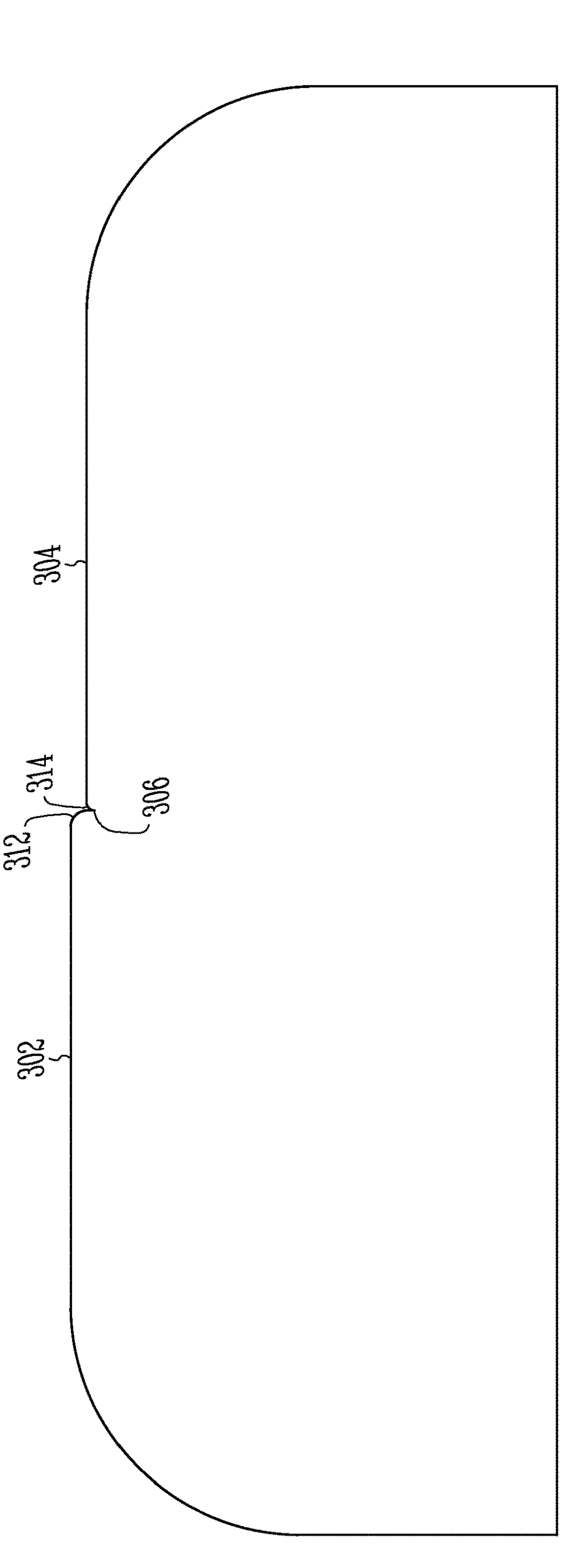

FIGS. 3A-3B show a portion of a header of an implantable medical device, in accordance with one embodiment. The header 300 include a first silicone portion 302 configured to surround a first portion of internal electronics of the header, and a second silicone portion 304 configured to surround a second portion of internal electronics of the header. The header 300 can further include a splitline 306 where the first silicone portion abuts the second silicone portion, wherein an outer edge 312 of the first silicone portion and an outer edge 314 of the second silicone portion are rounded at the splitline to prevent a sharp edge that may cause damage during assembly or insertion.

According to various embodiments, the outer edge of the first silicone portion and the outer edge of the second silicone portion are rounded to an angle of radius greater than 8 thou at the splitline. The outer edge of the first silicone portion and the outer edge of the second silicone portion are rounded to a radius of greater than 10 thou at the splitline, in various embodiments. In some embodiments, the outer edge of the first silicone portion and the outer edge of the second silicone portion are rounded to a radius of greater than 15 thou at the splitline. The outer edge of the first silicone portion and the outer edge of the second silicone portion are indented at the splitline, in some examples. In various examples, the outer edge of the first silicone portion and the outer edge of the second silicone portion are machined at the splitline. The outer edge of the first silicone portion and the outer edge of the second silicone portion include a radius undercut feature at the splitline, in various examples.

Figures 4A, 4B:
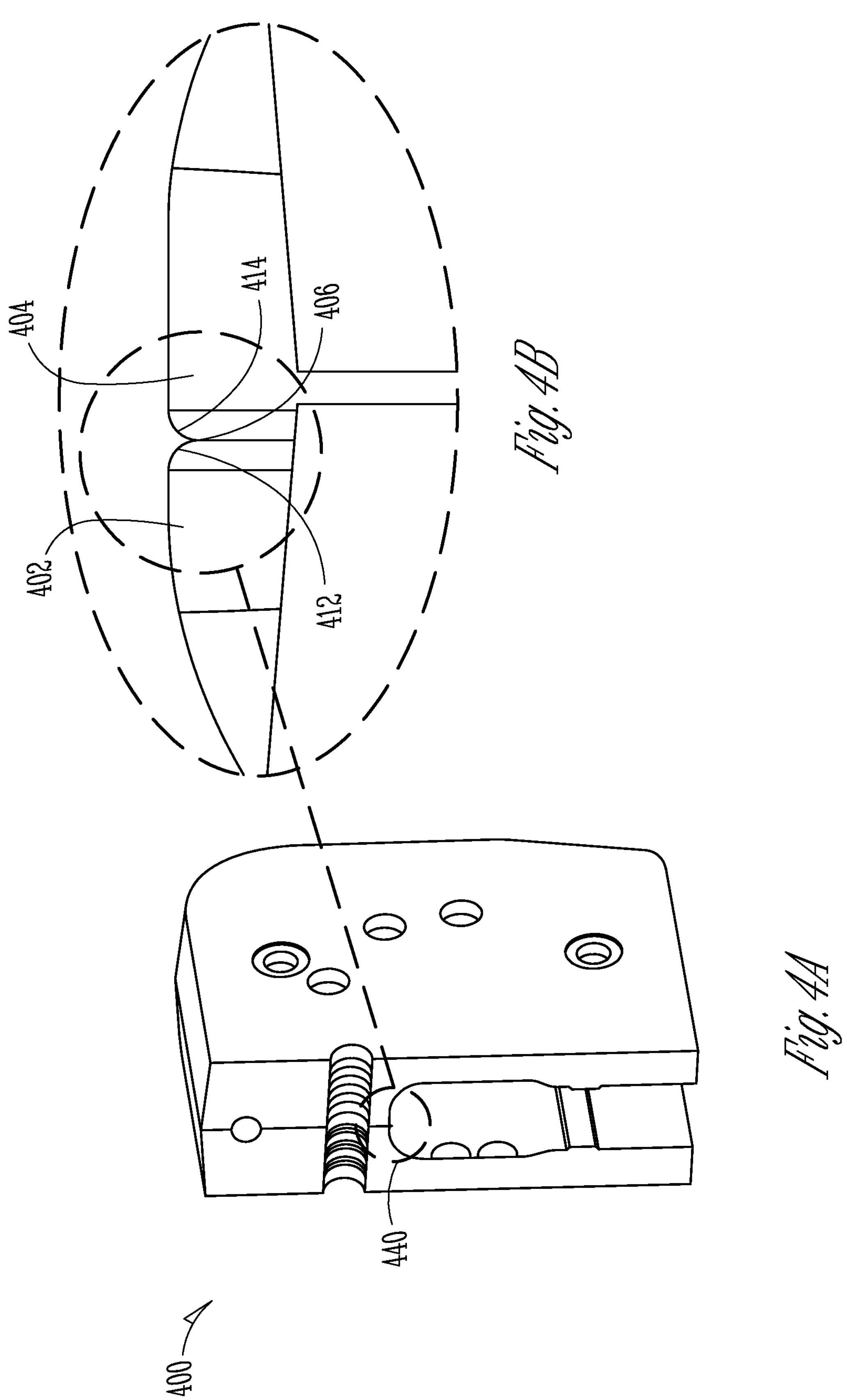
FIGS. 4A-4B show views of a portion of an implantable medical device, in accordance with one embodiment.

FIGS. 4A-4B show views of a portion of an implantable medical device, in accordance with one embodiment. FIG. 4A illustrates an implantable medical device having a header 400. FIG. 4B is an exploded view of area 440 of the header 400. The header 400 include a first silicone portion 402 configured to surround a first portion of internal electronics of the header, and a second silicone portion 404 configured to surround a second portion of internal electronics of the header. The header 400 can further include a splitline 406 where the first silicone portion abuts the second silicone portion, wherein an outer edge 412 of the first silicone portion and an outer edge 414 of the second silicone portion are rounded at the splitline to prevent a sharp edge that may cause damage during assembly or insertion.

Figure 5:
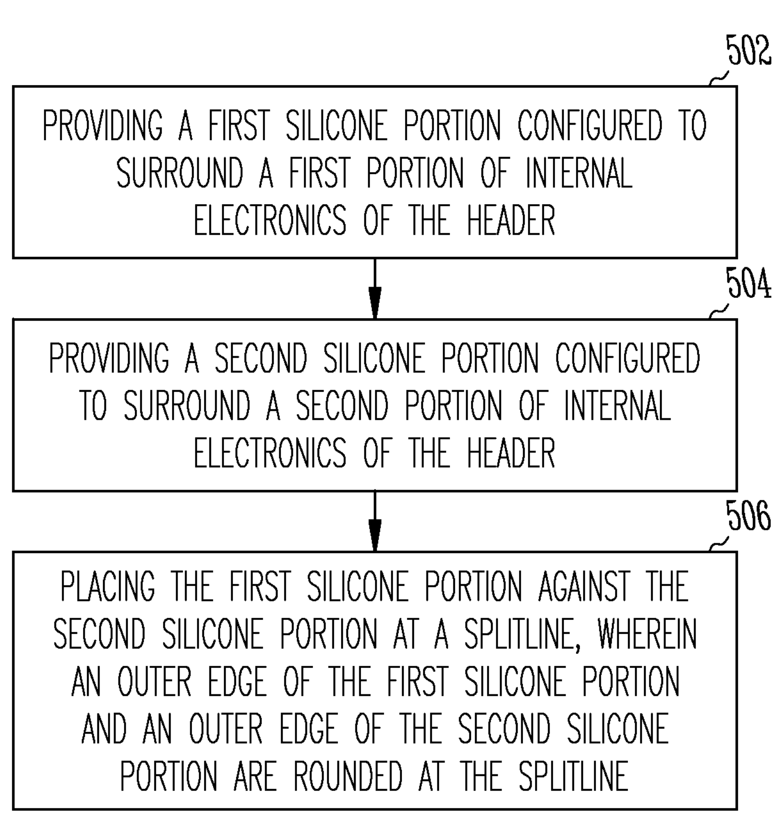
FIG. 5 shows a method of assembling a header for a medical device, in accordance with one embodiment.

FIG. 5 shows a method of assembling a header for a medical device, in accordance with one embodiment. The method 500 includes providing a first silicone portion configured to surround a first portion of internal electronics of the header, at step 502, and providing a second silicone portion configured to surround a second portion of internal electronics of the header, at step 504. The method 500 further includes placing the first silicone portion against the second silicone portion at a splitline, wherein an outer edge of the first silicone portion and an outer edge of the second silicone portion are rounded at the splitline, at step 506.

The present device, system and method can provide for manufacturing of header to ensure tolerance and alignment of silicone portions to prevent sharp edges that can cause damage or injury upon assembly or device placement. In addition, the present subject matter can provide for mitigation of potential damage to a lead during insertion and improved perception of the device.

Two silicone portions that mate together may form a sharp edge that causes insertion issues. In various embodiments, the header cavity is inserted into tooling that normally may be one piece using two materials, and the present subject matter provides for radii on edges of the two portions with a mismatch to prevent any sharp edges. This subject matter provides benefits such as avoiding cutting sutures or leads, and further results in a smooth interior of the device without having to buff and polish a surface of the header.

The present subject matter provides for radius edges where before there were sharp corners, in various embodiments. No polishing is needed to remove the sharp edges, in various examples. In addition, the present subject matter provides a recess inward which cannot be achieved with polishing. This inward recess is provided by having a radius undercut feature on the silicone mould halves which are used to make the header, in various embodiments. In various examples, the silicone moulds are two halves which are mated together before moulding the epoxy, thus resulting in a splitline.

In various examples, the header includes a clear material or skin with two silicone preforms (left hand side LHS and right hand side RHS) with a negative profile that are epoxied together or joined at a splitline. The present subject matter provides for smooth edges even with a mismatch and without trimming, by providing a negative radius at the edge of each of the LHS and RHS portions, to present an indented or rounded seam at the splitline that is not sharp. In various examples, the feature has a radius of 8 thou or higher. In other examples, the feature has a radius of 10 thou or 15 thou. Other radii may be used without departing from the scope of the present subject matter. The inserts or preforms may be machined together or separately, in various examples. The radius of the meeting of the portions at the splitline provides for rounded edges that do not need to be trimmed or polished and will not damage the lead, sutures or body upon insertion, in various examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A header for a medical device, the header comprising:

a first silicone portion configured to surround a first portion of internal electronics of the header;

a second silicone portion configured to surround a second portion of internal electronics of the header; and a splitline where the first silicone portion abuts the second silicone portion, wherein an outer edge of the first silicone portion and an outer edge of the second silicone portion are rounded outward at the splitline.

2. The header of claim 1, wherein the outer edge of the first silicone portion and the outer edge of the second silicone portion are rounded to a radius of greater than 8 thou at the splitline.

3. The header of claim 1, wherein the outer edge of the first silicone portion and the outer edge of the second silicone portion are rounded to a radius of greater than 10 thou at the splitline.

4. The header of claim 1, wherein the outer edge of the first silicone portion and the outer edge of the second silicone portion are rounded to a radius of greater than 15 thou at the splitline.

5. The header of claim 1, wherein the outer edge of the first silicone portion and the outer edge of the second silicone portion are indented at the splitline.

6. The header of claim 1, wherein the outer edge of the first silicone portion and the outer edge of the second silicone portion are machined at the splitline.

7. The header of claim 1, wherein the outer edge of the first silicone portion and the outer edge of the second silicone portion include a radius undercut feature at the splitline.

8. The header of claim 1, wherein the outer edge of the first silicone portion and the outer edge of the second silicone portion are convexly rounded outward the splitline to prevent sharp edges at the splitline that can cause damage during assembly or use.

9. The header of claim 1, wherein the outer edge of the first silicone portion and the outer edge of the second silicone portion are rounded outward at and perpendicular to the splitline to prevent sharp edges at the splitline that can cause damage during assembly or use.

10. An implantable medical device comprising:

a housing including electronic devices within the housing; and a header attached to the housing, the header including:

a first silicone portion configured to surround a first portion of internal electronics of the header;

a second silicone portion configured to surround a second portion of internal electronics of the header; and a splitline where the first silicone portion abuts the second silicone portion, wherein an outer edge of the first silicone portion and an outer edge of the second silicone portion are rounded outward at the splitline.

11. The implantable medical device of claim 10, wherein the outer edge of the first silicone portion and the outer edge of the second silicone portion are rounded to a radius of greater than 8 thou at the splitline.

12. The implantable medical device of claim 10, wherein the outer edge of the first silicone portion and the outer edge of the second silicone portion are rounded to a radius of greater than 10 thou at the splitline.

13. The implantable medical device of claim 10, wherein the outer edge of the first silicone portion and the outer edge of the second silicone portion are rounded to a radius of greater than 15 thou at the splitline.

14. The implantable medical device of claim 10, wherein the outer edge of the first silicone portion and the outer edge of the second silicone portion are indented at the splitline.

15. The implantable medical device of claim 10, wherein the outer edge of the first silicone portion and the outer edge of the second silicone portion are machined at the splitline.

16. The implantable medical device of claim 10, wherein the outer edge of the first silicone portion and the outer edge of the second silicone portion include a radius undercut feature at the splitline.

17. A method of assembling a header for a medical device, the method comprising:

providing a first silicone portion configured to surround a first portion of internal electronics of the header;

providing a second silicone portion configured to surround a second portion of internal electronics of the header; and placing the first silicone portion against the second silicone portion at a splitline, wherein an outer edge of the first silicone portion and an outer edge of the second silicone portion are rounded outward at the splitline.

18. The method of claim 17, wherein the outer edge of the first silicone portion and the outer edge of the second silicone portion are rounded to a radius of greater than 8 thou at the splitline.

19. The method of claim 17, wherein the outer edge of the first silicone portion and the outer edge of the second silicone portion are rounded to a radius of greater than 10 thou at the splitline.

20. The method of claim 17, wherein the outer edge of the first silicone portion and the outer edge of the second silicone portion are rounded to a radius of greater than 15 thou at the splitline.

* * * * *